United States Patent [19]

Ratton

[11] Patent Number: 4,487,975
[45] Date of Patent: Dec. 11, 1984

[54] ETHERIFICATION OF PHENOLS

[75] Inventor: Serge Ratton, La Verpilliere, France

[73] Assignee: Rhone-Poulenc Industries, Paris, France

[21] Appl. No.: 407,059

[22] Filed: Aug. 11, 1982

Related U.S. Application Data

[63] Continuation-in-part of Ser. No. 247,372, Mar. 25, 1981, abandoned.

[30] Foreign Application Priority Data

Mar. 31, 1980 [FR] France .............................. 80 07628
Sep. 29, 1981 [FR] France .............................. 81 18571

[51] Int. Cl.³ ............................................. C07C 41/16
[52] U.S. Cl. ...................................... 568/587; 568/433; 568/586; 568/633; 568/650; 568/652; 568/653; 568/636; 260/465 F; 564/443

[58] Field of Search .............. 568/650, 652, 653, 633, 568/636, 586, 587, 433; 260/465 F; 564/443

[56] References Cited

U.S. PATENT DOCUMENTS 3,911,022 10/1975 McCloud et al. .............. 568/651 X
4,153,810 5/1979 Neumann et al. .............. 568/650 X

FOREIGN PATENT DOCUMENTS 46-11494 3/1971 Japan ................................. 568/630

Primary Examiner—Bernard Helfin
Attorney, Agent, or Firm—Burns, Doane, Swecker & Mathis

[57] ABSTRACT

Phenols, including the polyhydric phenols, are selectively monoetherified with an alkyl or alkenyl carboxylate, or admixture of compounds adapted to in situ form such carboxylate, in the presence of a salt of a carboxylic acid.

52 Claims, No Drawings

ETHERIFICATION OF PHENOLS

CROSS-REFERENCE TO RELATED APPLICATION

This application is a continuation-in-part of my earlier copending application Ser. No. 247,372, filed Mar. 25, 1981, now abandoned, which is hereby expressly incorporated by reference herein and relied upon.

BACKGROUND OF THE INVENTION

1. Field of the Invention

The present invention relates to the improved etherification of phenols, and, more especially, to the selective etherification of phenolic compounds which can even contain a plurality of hydroxy functions.

2. Description of the Prior Art

It is known to this art to etherify phenols by means of an alkyl sulfate or an alkyl halide (Houben-Weyl, *Methoden der Organischen Chemie* [Methods of Organic Chemistry], Volume III, page 54 (1965).

Such method can make it possible to selectively obtain a monoether, when stoichiometric amounts of reactants are used. However, the reactants used are expensive and, moreover, the reaction gives rise to the preparation of inorganic salts which present serious problems of corrosion of the apparatus and toxicity of the effluents.

Recently, published Japanese Patent Application No. 79/030,123 has disclosed that it is possible to etherify the phenol groups of dihydroxy aromatic compounds by reaction with alkyl phosphates; however, it is not possible to prevent significant dietherification reaction.

U.S. Pat. No. 3,911,022 describes a process for the etherification of phenolic compounds having one or more hydroxyl groups, by means of a saturated aliphatic alcohol having 1 to 4 carbon atoms or an ester of an alcohol of this type with a saturated aliphatic carboxylic acid, in the presence of an aliphatic tertiary amine or of a chloride, a sulfate or a carboxylate of an amine of this type. However, it has also been demonstrated that, when such process is applied to a dihydric phenol, a mixture of monoethers and diethers necessarily results.

Finally, U.S. Pat. No. 4,153,810 describes a process for the preparation of alkyl/aryl ethers by reacting an hydroxylated aromatic compound with an aliphatic alcohol, in the presence of strongly acid cation exchange resins, such process being characterized in that the reaction is carried out utilizing at least 3 mols of hydroxylated aromatic compound per mol of aliphatic alcohol. The temperature at which the process is carried out preferably ranges from 110° C. to 130° C. This process makes it possible to selectively obtain the monoether from a polyphenol. But a very serious disadvantage of a process of this type is in the high cost of the resins used as catalyst, and in their sensitivity to heat, which is likely to cause their degradation.

SUMMARY OF THE INVENTION

Accordingly, a major object of the present invention is the provision of an improved process for the selective, or monoetherification of phenols, even polyhydric phenols, which process features inexpensive reactants and which otherwise avoids those disadvantages and drawbacks to date characterizing this art.

The subject etherification is referred to as "selective" because only a single phenol group is etherified, even in the event the phenolic reactant contains a plurality of hydroxyl functions on the same aromatic ring.

Briefly, the present invention features the improved etherification of one hydroxyl function of a phenolic compound having the general formula:

$$HO-Ar-(R)_n \qquad (I)$$

in which: Ar represents an aromatic radical consisting of a benzene ring or of a structure formed by several ortho-fused or ortho- and peri-fused benzene rings, e.g., naphthalene, anthracene or phenanthrene; the substituents R, which are identical or different, represent a hydroxyl group, a linear or branched chain alkyl radical having from 1 to 6 carbon atoms, a linear or branched chain alkenyl radical having from 2 to 6 carbon atoms, a phenyl radical optionally substituted with one or more alkyl radicals each having 1 to 4 carbon atoms, a cycloalkyl radical containing 5 or 6 carbon atoms optionally substituted with one or more alkyl radicals each having 1 to 4 carbon atoms, a phenylalkyl radical in which the aliphatic chain contains 1 to 4 carbon atoms, a cycloalkyl-alkyl radical in which the cycloalkyl portion contains 5 or 6 carbon atoms and the aliphatic chain contains from 1 to 4 carbon atoms, a halogen atom, a nitro group, an amine group, an aldehyde group, —CHO, or a nitrile group; and n is a number from 0 to 5; comprising reacting such compound (I) with an etherification agent selected from the group comprising alkyl carboxylates, the linear or branched chain alkyl radical having 1 to 6 carbon atoms, alkenyl carboxylates, the linear or branched chain alkenyl radical having 3 to 6 carbon atoms, and compounds capable of forming these carboxylates, and such reaction being characterized in that same is carried out in the presence of a carboxylic acid salt.

The invention can also be deemed a process for the preparation of phenol monoethers by reacting a compound of the general formula (I) with an etherification agent selected from the group comprising alkyl carboxylates, the linear or branched chain alkyl radical having 1 to 6 carbon atoms, alkenyl carboxylates, the linear or branched chain alkenyl radical having 3 to 6 carbon atoms, and compounds capable of forming these carboxylates, and said process being characterized in that the reaction is carried out in the presence of a carboxylic acid salt.

DETAILED DESCRIPTION OF THE INVENTION

More particularly according to this invention, the reactant phenols (I) are preferably those in which the radical Ar corresponds to benzene, naphthalene, anthracene or phenanthrene, the substituents R, which are identical or different, represent a hydroxyl group, a linear or branched chain alkyl radical having 1 to 4 carbon atoms, such as methyl, ethyl, isopropyl, n-propyl, n-butyl, isobutyl or tert.-butyl, a linear or branched chain alkenyl radical having 2 to 4 carbon atoms, such as vinyl, allyl, prop-1-enyl, isopropenyl, but-1-enyl, but-2-enyl, but-3-enyl, 1-methylprop-1-enyl, 1-methylprop-2-enyl, 2-methylprop-1-enyl or 2-methylprop-2-enyl, an optionally substituted phenyl radical, an optionally substituted cyclohexyl radical, a phenylalkyl radical in which the aliphatic chain contains from 1 to 3 carbon atoms, such as benzyl, phenethyl, phenylpropyl or phenylisopropyl, a cyclohexylalkyl radical in which the aliphatic chain contains 1 to 3 carbon atoms, a chlorine atom, a bromine atom or a nitro group, and n is an integer from 0 to 3.

Exemplary of phenol compounds of this type which are representative are:

Monophenols, such as phenol, 1-naphthol, 2-naphthol, 1-phenanthrol, 2-phenanthrol, 3-phenanthrol, 9-phenanthrol, 1-anthrol, 2-anthrol and 9-anthrol;

Diphenols, such as resorcinol, pyrocatechol, hydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, 1,2-dihydroxyanthracene, 1,5-dihydroxyanthracene, 1,8-dihydroxyanthracene, 2,6-dihydroxyanthracene, 9,10-dihydroxyanthracene and 3,4-dihydroxyphenanthrene;

Triphenols, such as pyrogallol, 1,2,4-trihydroxybenzene, 1,3,5-trihydroxybenzene, 1,2,9-trihydroxyanthracene, 1,2,10-trihydroxyanthracene, 1,4,9-trihydroxyanthracene, 1,5,9-trihydroxyanthracene, 1,8,9-trihydroxyanthracene, 2,3,9-trihydroxyanthracene and 3,4,5-trihydroxyphenanthrene; and Monophenols or diphenols additionally bearing 1 or more other substituents R, such as 2-chlorophenol, 3-chlorophenol, 4-chlorophenol, 2-bromophenol, 3-bromophenol, 4-bromophenol, 2-nitrophenol, 3-nitrophenol, 4-nitrophenol, 2-methylphenol, 3-methylphenol, 4-methylphenol, 2-ethylphenol, 3-ethylphenol, 4-ethylphenol, 2-isopropylphenol, 3-isopropylphenol, 4-isopropylphenol, 2-propylphenol, 3-propylphenol, 4-propylphenol, 4-(prop-1-enyl)phenol, 2-allylphenol, 4-allylphenol, 3-butylphenol, 4-butylphenol, 4-isobutylphenol, 2-tert.-butylphenol, 3-tert.-butylphenol, 4-tert.-butylphenol, 2-benzylphenol, 4-benzylphenol, 2-cyclohexylphenol, 2,3-dichlorophenol, 2,4-dichlorophenol, 2,5-dichlorophenol, 2,6-dichlorophenol, 3,4-dichlorophenol, 3,5-dichlorphenol, 1,2-dimethyl-3-hydroxybenzene, 1,2-dimethyl-4-hydroxybenzene, 1,3-dimethyl-5-hydroxybenzene, 1,3-dimethyl-2-hydroxybenzene, 1,4-dimethyl-2-hydroxybenzene, 2,4-dimethyl-1-hydroxybenzene, 1-tert.-butyl-2-hydroxy-4-methylbenzene, 2-tert.-butyl-1-hydroxy-4-methylbenzene, 2-tert.-butyl-4-ethyl-1-hydroxybenzene, 4-tert.-butyl-2-ethyl-1-hydroxybenzene, 1,3-di-tert.-butyl-2-hydroxybenzene, 2,4-di-tert.-butyl-1-hydroxybenzene, 2-hydroxy-4-isopropyl-1-methylbenzene, 2-allyl-4-chloro-1-hydroxybenzene, 1-hydroxy-2,4,5-trimethylbenzene, 2-hydroxy-1,3,5-trimethylbenzene, 2-hydroxy-1,3,5-tri-tert.-butylbenzene, 1,3-di-tert.-butyl-2-hydroxy-5-methylbenzene, 1,5-di-tert.-butyl-2-hydroxy-3-methylbenzene, 1,5-di-tert.-butyl-2-hydroxy-4-methylbenzene, 1-tert.-butyl-2,5-dimethyl-4-hydroxybenzene, 1-tert.-butyl-3,5-dimethyl-2-hydroxybenzene, 1-tert.-butyl-4,5-dimethyl-2-hydroxybenzene, 5-tert.-butyl-1,3-dimethyl-2-hydroxybenzene, 1-chloro-2,3-dimethyl-4-hydroxybenzene, 1-chloro-2,3-dimethyl-5-hydroxybenzene, 1-chloro-2,4-dimethyl-5-hydroxybenzene, 1-chloro-2,5-dimethyl-4-hydroxybenzene, 1-chloro-3,4-dimethyl-2-hydroxybenzene, 1-chloro-4,5-dimethyl-2-hydroxybenzene, 2-chloro-1,3-dimethyl-5-hydroxybenzene, 2-chloro-1,5-dimethyl-3-hydroxybenzene, 2-chloro-3,4-dimethyl-1-hydroxybenzene, 5-chloro-1,3-dimethyl-2-hydroxybenzene, 1,2-dimethyl-3-hydroxy-5-nitrobenzene, 1,2-dimethyl-4-hydroxy-5-nitrobenzene, 1,3-dimethyl-2-hydroxy-4-nitrobenzene, 1,3-dimethyl-2-hydroxy-5-nitrobenzene, 1,4-dimethyl-2-hydroxy-3-nitrobenzene, 1,4-dimethyl-2-hydroxy-5-nitrobenzene, 1,5-dimethyl-2-hydroxy-3-nitrobenzene, 1,5-dimethyl-3-hydroxy-2-nitrobenzene, 2,5-dimethyl-1-hydroxy-3-nitrobenzene, 8-nitro-1-naphthol, 1-nitro-2-naphthol, 5-nitro-2-naphthol, 1-methyl-2-naphthol, 1-bromo-2,4-dihydroxybenzene, 1-bromo-3,5-dihydroxybenzene, 2-bromo-1,3-dihydroxybenzene, 2-bromo-1,4-dihydroxybenzene, 4-bromo-1,2-dihydroxybenzene, 1-butyl-2,4-dihydroxybenzene, 1-chloro-2,3-dihydroxybenzene, 1-chloro-2,4-dihydroxybenzene, 1-chloro-3,5-dihydroxybenzene, 2-chloro-1,3-dihydroxybenzene, 2-chloro-1,4-dihydroxybenzene, 4-chloro-1,2-dihydroxybenzene, 2,4-dihydroxy-1-ethylbenzene, 2,4-dihydroxy-1-isobutylbenzene, 1,2-dihydroxy-4-isopropylbenzene, 1,4-dihydroxy-2-isopropylbenzene, 2,4-dihydroxy-1-isopropylbenzene, 2,3-dihydroxy-1-isopropyl-4-methylbenzene, 1,4-dihydroxy-2-isopropyl-5-methylbenzene, 1,2-dihydroxy-3-methylbenzene, 1,3-dihydroxy-2-methylbenzene, 1,3-dihydroxy-2-nitrobenzene, 1,4-dihydroxy-2-nitrobenzene, 1,2-dihydroxy-4-propylbenzene, 1,3-dihydroxy-5-propylbenzene, 2,4-dihydroxy-1-propylbenzene, 1,2-dichloro-4,5-dihydroxybenzene, 1,3-dichloro-2,5-dihydroxybenzene, 1,4-dichloro-2,5-dihydroxybenzene, 1,5-dichloro-2,3-dihydroxybenzene, 1,5-dichloro-2,4-dihydroxybenzene, 2,3-dichloro-1,4-dihydroxybenzene, 1,2-dihydroxy-3,5-dimethylbenzene, 1,2-dihydroxy-4,5-dimethylbenzene, 1,3-dihydroxy-2,4-dimethylbenzene, 1,3-dihydroxy-2,5-dimethylbenzene, 1,4-dihydroxy-2,3-dimethylbenzene, 1,4-dihydroxy-2,5-dimethylbenzene, 1,5-dihydroxy-2,4-dimethylbenzene, 1,5-dihydroxy-3,4-dimethylbenzene, 2,5-dihydroxy-1,3-dimethylbenzene and 1,3-dihydroxy-2,4-dinitrobenzene.

The subject process more preferably entails the selective etherification of phenol, 1-naphthol, 2-naphthol, 2-methylphenol, 3-methylphenol, 4-methylphenol, monochlorophenols, dichlorophenols and monoethylphenols; and of diphenols and triphenols such as pyrocatechol, resorcinol, hydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene and 2,7-dihydroxynaphthalene. Indeed, in a particularly preferred embodiment of the present invention, the subject process entails selective monoetherification of phenol compounds of formula (I) in which Ar represents benzene or naphthalene; the substituents R, which are identical or different, represent a hydroxyl group, a linear or branched chain alkyl radical having 2 to 4 carbon atoms, a linear or branched chain alkenyl radical having 2 to 4 carbon atoms, a chlorine atom, a bromine atom or a nitro group, at least one of R being a hydroxyl group; and n is 1, 2 or 3.

Exemplary of these particularly preferred phenol compounds are:

resorcinol, pyrocatechol, hydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, pyrogallol, 1,2,4-trihydroxybenzene, 1-bromo-2,4-dihydroxybenzene, 1-bromo-3,5-dihydroxybenzene, 2-bromo-1,3-dihydroxybenzene, 2-bromo-1,4-dihydroxybenzene, 4-bromo-1,2-dihydroxybenzene, 1-butyl-2,4-dihydroxybenzene, 1-chloro-2,3-dihydroxybenzene, 1-chloro-2,4-dihydroxybenzene, 1-chloro-3,5-dihydroxybenzene, 2-chloro-1,3-dihydroxybenzene, 2-chloro-1,4-dihydroxybenzene, 4-chloro-1,2-dihydroxybenzene, 2,4-dihydroxy-1-ethylbenzene, 2,4-dihydroxy-1-isobutylbenzene, 1,2-dihydroxy-4-isopropylbenzene, 1,4-dihydroxy-2-isopropylbenzene, 2,4-dihydroxy-1-isopropylbenzene, 2,3-dihydroxy-1-isopropyl-4-methylbenzene, 1,4-dihydroxy-2-isopropyl-5-methylbenzene, 1,2-dihydroxy-3-methylbenzene, 1,3-dihydroxy-2-methylbenzene, 1,3-dihydroxy-2-nitrobenzene, 1,4-dihydroxy-2-nitrobenzene, 1,2-dihydroxy-4-propylbenzene, 1,3-dihydroxy-5-propylbenzene, 2,4-dihydroxy-1-propylbenzene, 1,2-dichloro-4,5-dihydroxybenzene, 1,3-dichloro-2,5-dihydroxybenzene, 1,4-dichloro-2,5-dihydroxybenzene, 1,5-dichloro-2,3-dihydroxybenzene, 1,5-dichloro-2,4-dihydroxybenzene, 2,3-dichloro-1,4-dihydroxybenzene, 1,2-dihydroxy-3,5-dimethylbenzene, 1,2-dihydroxy-4,5-dimethylbenzene, 1,3-dihydroxy-2,4-dimethylbenzene, 1,3-dihydroxy-2,5-dimethylbenzene, 1,4-dihydroxy-2,3-dimethylbenzene, 1,4-dihydroxy-2,5-dimethylbenzene, 1,5-dihydroxy-2,4-dimethylbenzene, 1,5-dihydroxy-3,4-dimethylbenzene, 2,5-dihydroxy-1,3-dimethylbenzene, and 1,3-dihydroxy-2,4-dinitrobenzene.

The concentration of the phenol compound of the formula (I) in the reaction medium is not critical. It varies very widely, in particular according to the solubility of such compound in said reaction medium, which consists of the etherification agent, the carboxylic acid salt and, if appropriate, other constituents more fully described hereinbelow and which can consist, in particular, of adjuvants which are not essential but which assist in carrying out the process according to the invention and/or of an auxiliary solvent.

For reasons of convenience, the concentration of the phenolic compound (I) will be expressed relative to the liquid medium, namely, relative to the reaction medium excluding the phenolic compound itself and the carboxylic acid salt.

Thus, typically, the reaction is carried out with from 1% to 50% by weight of the phenolic compound (I), relative to the volume of the liquid medium. Most frequently, this concentration is between 2% and 30% by weight per volume.

Among the etherification agents which are useful in the process according to the invention, there are mentioned as representative, in particular, the esters of monofunctional saturated or unsaturated aliphatic carboxylic acids containing, in particular, 2 to 18 carbon atoms, or polyfunctional saturated or unsaturated aliphatic carboxylic acids containing, in particular, 3 to 18 carbon atoms, of monofunctional or polyfunctional aromatic carboxylic acids, of monofunctional or polyfunctional arylaliphatic carboxylic acids or of monofunctional or polyfunctional cycloaliphatic carboxylic acids with alcohols such as methanol, ethanol, n-propanol, isopropanol, butan-1-ol, butan-2-ol, tert.-butanol, prop-2-en-1-ol, 2-methylprop-2-en-1-ol, but-2-en-1-ol, but-3-en-1-ol or but-3-en-2-ol.

It is also envisaged to use compounds which are capable of forming such esters in situ, and in particular a mixture of an alcohol such as those listed above with a carboxylic acid such as those defined above. This embodiment of the invention is preferred, especially for reasons of convenience, these reactants ofttimes being more readily available than the esters themselves. Moreover, it is not necessary to utilize stoichiometric amounts of alcohol and of carboxylic acid. Finally, the etherification reaction is generally more rapid with these reactants than with the esters. The molar ratio alcohol/carboxylic acid can also vary over wide limits, for example, between 0.02 and 50, and more advantageously between 0.1 and 40. The molar ratio carboxylic acid/phenol compound can also vary very widely. In general, it is between 0.1 and 100. This ratio is preferably between 0.5 and 50.

In the following text, when "etherification agent" is mentioned, this term will encompass both the ester itself and the mixtures, in the proportions defined above, of the corresponding alcohol and the corresponding carboxylic acid.

The amount of etherification agent employed is typically selected such that the molar ratio of the ester and/or alcohol forming part of the composition of the said etherification agent to the phenol compound of the formula (I) is greater than or equal to 0.5 and preferably is greater than or equal to 1.

By way of illustration of the above carboxylic acids, representative are saturated aliphatic monoacids, such as acetic acid, propanoic acid, n-butanoic acid, 2-methylpropanoic acid, n-pentanoic acid, 2-methylbutanoic acid, 3-methylbutanoic acid, 3,3-dimethylbutanoic acid, n-hexanoic acid, 2-methylpentanoic acid, 3-methylpentanoic acid and 4-methylpentanoic acid; unsaturated aliphatic monoacids, such as propenoic acid, but-2-enoic acid, 2-methylpropenoic acid, but-3-enoic acid, cis-2-methylbut-2-enoic acid (angleic acid), trans-2-methylbut-2-enoic acid (tiglic acid), pent-4-enoic acid, hex-3-enoic acid and hex-4-enoic acid; saturated aliphatic diacids, such as malonic acid, succinic acid, glutaric acid and adipic acid; ethylenic diacids, such as maleic acid and fumaric acid; aromatic monoacids or diacids, such as benzoic acid, orthophthalic acid, isophthalic acid, terephthalic acid, mononitrobenzoic acids and monochlorobenzoic acids; arylaliphatic acids, such as phenylacetic acid, 2-phenylpropanoic acid and 4-phenylpropanoic acid; and cycloaliphatic acids, such as cyclohexane-1,3-dicarboxylic acid and cyclohexane-1,4-dicarboxylic acid.

It too is envisaged to use mixtures comprising a carboxylic acid ester and the corresponding free alcohol or a carboxylic acid ester with the free alcohol and the free carboxylic acid corresponding to this ester. Also in the present text, when "etherification agent" is noted, it is to be understood that it can mean a mixture of this type, without it being necessary to specify such fact on each occasion.

The etherification agents which are preferably used are the esters of methanol, ethanol, n-propanol, prop-2-en-1-ol and 2-methylprop-2-en-1-ol and of a carboxylic acid, or the mixtures, as defined above, of one of these alcohols with a carboxylic acid. The carboxylic acid is advantageously selected from among monofunctional or difunctional saturated aliphatic acids having 2 to 6 carbon atoms, benzoic acid and orthophthalic, metaphthalic or terephthalic acids. Among these etherification agents, it is most preferred to use the acetates, the propionates and the succinates, or the mixtures consisting of acetic acid, propionic acid or succinic acid with one of the above-mentioned alcohols.

Finally, among these preferred etherification agents, it is more particularly preferred to employ the esters of methanol and the esters of ethanol, very especially their acetates or the mixtures consisting of methanol and one of the carboxylic acids or ethanol and one of the carboxylic acids, and very especially the mixtures consisting of one of these two alcohols with acetic acid.

The etherification agent can itself constitute the solvent medium in which the etherification reaction is carried out consistent with the process of the invention. However, of course, it is also possible to use an auxiliary solvent which is liquid under the conditions for carrying out the process, insofar as the said auxiliary solvent is inert towards the reactants and stable at the temperatures under which the reaction is carried out.

Water can be used as the auxiliary solvent. However, its presence provides a particular advantage and plays a remarkable role which is separate from the simple role of auxiliary solvent. In fact, the presence of water leads to an increase in the yield of the monoether of the phenolic compound and to a correlative decrease in the side reactions.

If the reaction is carried out in the presence of water, the latter can represent from 1% to 95% by volume of the liquid reaction medium. Preferably, the liquid reaction medium comprises from 20% to 80% by volume of water.

The carboxylic acid salt used as the catalyst in the process according to the invention can be any carboxylate, in particular alkali metal, ammonium and alkaline earth metal carboxylates. Exemplary of such carboxylates are sodium, potassium, lithium and ammonium carboxylates; calcium, magnesium and barium carboxylates may also be mentioned.

The carboxylic acids used to obtain these carboxylates can be monofunctional or polyfunctional saturated or unsaturated aliphatic carboxylic acids, monofunctional or polyfunctional aromatic carboxylic acids, monofunctional or polyfunctional arylaliphatic carboxylic acids or monofunctional or polyfunctional cycloaliphatic carboxylic acids, the rings of which can be substituted by one or more radicals.

These acids can be, for example, those which were mentioned hereinabove in the definition of the esters used as etherification agents.

Among all of the carboxylates which are useful herein, typically preferred are the salts of monofunctional saturated aliphatic carboxylic acids having from 2 to 6 carbon atoms, such as, in particular, acetic acid, propanoic acid, n-butanoic acid, n-pentanoic acid, n-hexanoic acid, 2-methylpropanoic acid, 2-methylbutanoic acid, 3-methylbutanoic acid, 3,3-dimethylbutanoic acid, 2-methylpentanoic acid, 3-methylpentanoic acid and 4-methylpentanoic acid, or of difunctional saturated aliphatic carboxylic acids having 3 to 6 carbon atoms, such as, in particular, malonic acid, succinic acid, glutaric acid and adipic acid, salts of benzoic acid and salts of ortho-phthalic, isophthalic and terephthalic acids. The alkali metal salts are the preferred salts of these acids.

Even more preferably, the sodium or potassium salts of these acids are employed. Among the latter salts, sodium acetate, sodium propionate and sodium succinate are most preferred.

The etherification agent and the carboxylic acid salt employed as the catalyst are conveniently selected such that they originate from (or contain) the same carboxylic acid, but this is not essential.

The amount of carboxylic acid salt present in the medium can vary over wide limits. If this amount is expressed relative to the phenolic compound, it is typically not less than 0.1 times the weight of the phenolic compound. The maximum amount is not critical. It does not usually exceed 50 times the weight of the phenolic compound. It is most typically preferred to use weight ratios carboxylic acid salt/phenolic compound which vary from 0.5 to 20.

Another advantageous embodiment consists of using a dicarboxylic acid of which one acid group is salified, in general by an alkali metal, and of which the other group is either free or esterified by an alcohol such as those mentioned above, most frequently methanol or ethanol.

An improvement to the process according to the present invention consists in using a catalytically effective amount of a metallic halide together with the salt of a carboxylic acid. This improved variation allows considerable shortening of the reaction time as compared to the basic process.

The metallic halide which can be used as a co-catalyst in this improved process is for example a metallic iodide. Generally, it is an alkali metal iodide such as sodium iodide, potassium iodide or lithium iodide; an alkaline earth metal iodide such as calcium iodide, magnesium iodide or barium iodide; or ammonium iodide. Among these iodides, sodium iodide and potassium iodide are most preferred.

The metallic halide and the salt of the carboxylic acid employed as the catalyst may contain the same alkali metal cation or they may contain different alkali metal cations.

The amount of metallic halide employed in the improved process can vary over wide limits. If this amount is expressed relative to the phenolic compound, it is generally between 0.1 to 50 times the weight of the phenolic compound. It is most typically preferred to use weight ratios metallic halide/phenolic compound which vary from 0.05 to 20.

The improved process of the invention employing a metallic halide co-catalyst is particularly preferred when combined with any of the various preferred embodiments of the basic process, e.g., when the starting material of formula (I) is a compound in which Ar represents benzene or naphthalene; the substituents R, which are identical or different, represent a hydroxyl group, a linear or branched chain alkyl radical having 2 to 4 carbon atoms, a chlorine atom, a bromine atom or a nitro group, at least one of R being a hydroxyl group; and n is 1, 2 or 3.

From a practical point of view, in order to obtain a very good yield of monoether, relative to the phenolic compound converted, while at the same time involving a relatively facile procedure and a relatively facile final treatment of the reaction medium, the following embodiment of the invention is preferably observed. The reaction is advantageously carried out in a medium consisting of the alcohol+carboxylic acid mixture which plays the dual role of reactant and solvent; water, most typically in an amount equal to that of the alcohol, and an alkali metal carboxylate, in particular the sodium carboxylate, derived from the free carboxylic acid used, are also added.

The relative amounts of the various reactants or constituents of the reaction mixture are then selected from within the preferred ranges indicated above.

To carry out the process according to the invention, it is necessary to heat the reactants; the temperature at which the reaction is carried out can vary from 150° C. to 350° C. It is preferably carried out between 220° C. and 300° C.

The pressure is not a critical parameter of the reaction. It usually consists of the autogenous pressure obtained by heating the reaction mixture to the desired temperature, in an appropriate closed apparatus. It is typically between 10 bars and 100 bars. However, it can attain higher values because it is possible, without departing from the scope of the invention, to create, in the apparatus used for the reaction, for example, by means of an inert gas such as nitrogen, an initial pressure, under cold conditions which is greater than atmospheric pressure.

The apparatus used is not specific to the process of the invention. It must simply exhibit certain characteristics: it must be able to withstand the pressures which are attained during heating, it must be leak-tight and obviously it must not be subject to attack from the reactants used.

In practice, the process according to the invention can be carried out in the following manner: the various constituents of the reaction mixture, such as defined above, are introduced into the appropriate apparatus. Same are then heated to the desired temperature, preferably while shaking or agitating the reaction vessel, although this is not really essential, for a period of time which can vary from a few minutes to more than 20 hours, for example. However, this period is typically on the order of a few hours, for example, from 2 hours to 10 hours, depending on the temperature at which the reaction is carried out. As mentioned earlier, shorter reaction times are possible when a metallic halide co-catalyst is employed, as compared to the basic process without a co-catalyst.

Upon completion of the reaction, the apparatus is cooled and the resultant reaction mass is treated in conventional manner, depending upon the reactants used; if the medium contains water, the organic compounds other than the carboxylic acid salt (and the metallic halide, if present) are extracted with a water-immiscible solvent. If the medium contains no water or very little water, it is usually possible to filter off the carboxylic acid salt (and the metallic halide, if present), either directly or after same has been precipitated by adding an organic solvent in which it is not soluble, but which dissolves the compounds formed during the reaction. It is also possible to add water to the medium before extracting the organic compounds.

The resulting products are separated off, in particular from the unconverted phenol compound, by operations which are common to this art, and are then analyzed, if necessary, also by methods which are well known to those skilled in this art.

The monoethers obtained by the process according to the invention can be used either directly or as intermediates for the synthesis of more complex organic compounds.

For example, 2-methoxyphenol (or guaiacol) is widely used in the pharmaceutical industry; it is also used as an intermediate for the preparation of vanillin.

In order to further illustrate the present invention and the advantages thereof, the following specific examples are given, it being understood that same are intended only as illustrative and in nowise limitative. In said examples all determinations were carried out by gas/liquid chromatography, unless stated otherwise.

EXAMPLE 1

The following reactants were introduced into a pressure-resistant glass tube:
Anhydrous sodium acetate: 9.18 g
Acetic acid: 0.75 g
Distilled water: 5 ml
Methanol: 5 ml
Pyrocatechol: 0.51 g The tube was sealed and was then heated to 250° C., under agitation, and maintained at such temperature for 5 hours.

Upon completion of the experiment, the tube was cooled and the unconverted pyrocatechol and the product guaiacol were extracted from the aqueous mixture with isopropyl ether. The products were analyzed by gas/liquid chromatography. The results were as follows:

Unconverted pyrocatechol: 0.344 g, i.e., a degree of conversion (DC) of the pyrocatechol of 32.5%.

Guaiacol formed: 0.190 g, i.e., a yield (Y) of 100%, relative to the pyrocatechol converted.

EXAMPLE 2

The following reactants were introduced into a pressure-resistant glass tube:
Anhydrous sodium acetate: 2.3 g
Acetic acid: 0.38 g
Distilled water: 5 ml
Methanol: 5 ml
Pyrocatechol: 0.501 g The tube was sealed and was then heated to 250° C., under agitation, and maintained at such temperature for 5 hours.

The final reaction mixture was treated and analyzed as in Example 1:
Unconverted pyrocatechol: 0.340 g—DC=32%
Guaiacol formed: 0.180 g—Y=about 100%

EXAMPLE 3

The following reactants were introduced into a pressure-resistant glass tube:
Anhydrous sodium acetate: 2.3 g
Acetic acid: 1.9 g
Distilled water: 5 ml
Methanol: 5 ml
Pyrocatechol: 0.5 g The experiment was carried out under the conditions of Example 1. The treatment of the final reaction mixture and the analysis thereof were also the same as in Example 1.

The following results were determined:
DC of the pyrocatechol: 34%
Y of guaiacol: 90%

Less than 5% (Y) of 1,2-dimethoxybenzene was detected by chromatography.

EXAMPLE 4

The following reactants were introduced into a pressure-resistant glass tube:
Anhydrous sodium acetate: 2.3 g
Acetic acid: 5.0 g
Distilled water: 5 ml
Methanol: 5 ml
Pyrocatechol: 0.5 g
The following results were determined:
DC of the pyrocatechol: 32%
Y of guaiacol: 95%

Less than 5% (Y) of 1,2-dimethoxybenzene was detected by chromatography.

EXAMPLE 5

The experiment was carried out as in Examples 1 and 2, but with the following reactants:
Anhydrous sodium acetate: 2.3 g Methyl acetate: 10 ml
Pyrocatechol: 0.5015 g The reaction was carried out under the same conditions as in Examples 1 and 2, except that the temperature was maintained at 250° for 4 hours, and the final mixture was analyzed as above after the addition of water and treatment identical to that of Example 1.

The results were as follows:
DC of the pyrocatechol: 2.3%
Y of guaiacol: 94.5%

No 1,2-dimethoxybenzene was detected by chromatography.

EXAMPLE 6

The following reactants were introduced into a pressure-resistant glass tube:
Anhydrous sodium acetate: 2.3 g
Methyl acetate: 5 ml
Distilled water: 5 ml
Pyrocatechol: 0.5004 g The tube was sealed and was then heated to 250° C., under agitation, and maintained at such temperature for 4 hours.

The final reaction mixture was treated and analyzed as in Example 1.

The results were as follows:
DC of pyrocatechol: 12.35%
Y of guaiacol: 100%

EXAMPLE 7

The following reactants were introduced into a pressure-resistant glass tube:
Anhydrous sodium acetate: 2.3 g
Acetic acid: 0.38 g
Distilled water: 2 ml
Methanol: 8 ml
Pyrocatechol: 0.501 g The experiment was carried out under the conditions of Example 1. The treatment of the final reaction mixture and the analysis thereof were also the same as in Example 1.

The following results were determined:
DC of the pyrocatechol: 75%
Y of guaiacol: 80%

About 5% (Y) of 1,2-dimethoxybenzene was detected by chromatography.

EXAMPLE 8

The following reactants were introduced into a pressure-resistant glass tube:
Anhydrous sodium acetate: 2.3 g
Acetic acid: 0.38 g
Distilled water: 8 ml
Methanol: 2 ml
Pyrocatechol: 0.5 g The experiment was carried out under the conditions of Example 1. The treatment of the final reaction mixture and the analysis thereof were also the same as in Example 1.

The following results were determined:
DC of the pyrocatechol: 25%
Y of guaiacol: 96%

Less than 3% (Y) of 1,2-dimethoxybenzene was detected by chromatography.

EXAMPLE 9

The following reactants were introduced into a pressure-resistant glass tube:
Anhydrous sodium acetate: 2.3 g
Acetic acid: 9 ml
Distilled water: 1 ml
Methanol: 5 ml
Pyrocatechol: 0.498 g The reaction was carried out as in Example 1.
The following results were determined:
DC of the pyrocatechol: 16%
Y of guaiacol: 100%

EXAMPLE 10

The following reactants were introduced into a pressure-resistant glass tube:
Anhydrous sodium acetate: 2.3 g
Acetic acid: 0.38 g
Methanol: 10 ml
Pyrocatechol: 0.5 g The reaction was carried out as in Example 1, but the temperature was maintained at 200° C. for 4 hours. The treatment of the final reaction mixture and the analysis thereof were the same as in Example 1 after the addition of water.

The following results were determined:
DC of the pyrocatechol: 24%
Y of guaiacol: 72%

Less than 5% (Y) of 1,2-dimethoxybenzene was detected by chromatography.

EXAMPLE 11

The following reactants were introduced into a pressure-resistant glass tube:
Anhydrous sodium acetate: 9.18 g
Acetic acid: 1.5 g
Methanol: 10 ml
Pyrocatechol: 0.5 g The reaction was carried out as in Example 1, but the temperature was maintained at 200° C. for 4 hours. The treatment of the final mixture and the analysis thereof were the same as in Example 1 after the addition of water.

The following results were determined:
DC of the pyrocatechol: 22%
Y of guaiacol: 67%

No 1,2-dimethoxybenzene was detected by chromatography.

EXAMPLE 12

The following reactants were introduced into a pressure-resistant glass tube:
Anhydrous sodium acetate: 2.3 g
Acetic acid: 0.38 g
Distilled water: 5 ml
Methanol: 5 ml
Phenol: 0.5 g The reaction was carried out as in Example 1.
The following results were determined:
DC of the phenol: 20%
Y of anisole (methoxybenzene): 75%

The presence of cresols or methylanisole was not detected.

EXAMPLE 13

The following reactants were introduced into a pressure-resistant glass tube:
Anhydrous sodium acetate: 2.3 g
Acetic acid: 0.38 g
Distilled water: 5 ml
Methanol: 5 ml Para-chlorophenol: 0.5 g
The reaction was carried out as in Example 1.
The following results were obtained:
DC of the para-chlorophenol: 37.8%
Y of para-chloroanisole: 52%

EXAMPLE 14

The following reactants were introduced into a pressure-resistant glass tube:
Acetic acid: 0.35 g
Sodium acetate: 2.3 g
Water: 5 ml
Ethanol: 5 ml
Pyrocatechol: 0.5 g The reaction was carried out as in Example 1.

Pyrocatechol monoethyl ether (guaiethol) was obtained with a selectivity (Y) of about 95%. The degree of conversion of the pyrocatechol was on the order of 15%.

The proportion of 1,2-diethoxybenzene was less than 2%.

EXAMPLE 15

The following reactants were introduced into a pressure-resistant glass tube:
Acetic acid: 1.5 g
Sodium acetate: 9.18 g
Water: 5 ml
Methanol: 5 ml
Hydroquinone: 1 g The reaction was carried out as in Example 1.

Hydroquinone monomethyl ether was obtained in a yield of about 95%, the degree of conversion of the hydroquinone being 10%. The virtually total absence of 1,4-dimethoxybenzene (amount of less than 2%) was noted.

EXAMPLE 16

The following reactants were introduced into a pressure-resistant glass tube:
Sodium acetate: 0.77 g
Potassium iodide: 0.77 g
Acetic acid: 0.26 g
Water: 3.4 ml
Methanol: 3.4 ml
Pyrocatechol: 1.56 g The reaction was carried out under the conditions of Example 1, but the tube was maintained at 250° C. for only 2 hours.

The final reaction mixture was treated and analyzed as in Example 1. The following results were determined:
DC of the pyrocatechol: 30%
Y of guaiacol: 97%
Y of 1,2-dimethoxybenzene: 3%

COMPARATIVE EXPERIMENTS

Experiment A:
The following reactants were introduced into a pressure-resistant glass tube:
Triethylamine: 0.5 g
Methyl acetate: 2.1 g
Methanol: 3.55 g
Pyrocatechol: 2.5 g The tube was sealed and then heated to 210° C., under agitation, and maintained at such temperature for 5 hours, 30 minutes.

After cooling, the final reaction mixture was analyzed by chromatography.
The following results were determined:
DC of the pyrocatechol: 59.5%
Y of guaiacol: 57%
Y of 1,2-dimethoxybenzene: 20%

No selectivity with respect to the monoether was observed.

Experiment B:
The following reactants were introduced into a pressure-resistant glass tube:
Triethylamine: 1.15 g
Methanol: 4.5 g
Acetic acid: 0.35 g
Pyrocatechol: 2.5 g The experiment was carried out under the same conditions as Experiment A and the final mixture was analyzed as above.

The following results were determined:
DC of the pyrocathechol: 64%
Y of guaiacol: 33%
Y of 1,2-dimethoxybenzene: 29%

No selectivity with respect to the monoether was observed.

Experiment C:
The following reactants were introduced into a pressure-resistant glass tube:
Triethylamine: 1.15 g
Methanol: 4.5 g
Acetic acid: 0.35 g
Water: 5 ml
Pyrocatechol: 2.5 g The experiment was carried out under the same conditions as Experiment A, but the temperature was maintained at 210° C. for a period of 5 hours. The treatment consisted of extracting the organic compounds with isopropyl ether. The resulting organic solution was analyzed by chromatography.

The following results were determined:
DC of the pyrocatechol: 22%
Y of guaiacol: 22.5%
Y of 1,2-dimethoxybenzene: 16.5%

No selectivity with respect to the monoether was observed.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the monoetherification of a phenol, comprising selectively monoetherifying a phenolic hydroxyl group of a compound having the structural formula (I):

HO—Ar—(R)$_n$     (I)

wherein Ar is an aryl radical comprising a benzene ring, or a plurality of ortho-fused or ortho- and peri-fused benzene rings; the substituents R, which are identical or different, represent a hydroxyl group, a linear or branched chain alkyl radical having from 1 to 6 carbon atoms, a linear or branched chain alkenyl radical having from 2 to 6 carbon atoms, a phenyl radical, a phenyl radical substituted with one or more alkyl radicals each having 1 to 4 carbon atoms, a cycloalkyl radical containing 5 or 6 carbon atoms, a cycloalkyl radical containing 5 or 6 carbon atoms and substituted with one or more alkyl radicals each having 1 to 4 carbon atoms, a phenylalkyl radical in which the aliphatic chain contains 1 to 4 carbon atoms, a cycloalkyl-alkyl radical in which the cycloalkyl portion contains 5 or 6 carbon atoms and the aliphatic chain contains from 1 to 4 carbon atoms, a halogen atom, a nitro atom, an amine group, an aldehyde group or a nitrile group, at least one of the substituents R being a hydroxyl group; and n is a number ranging from 1 to 5; with an alkyl or alkenyl carboxylate, or admixture of compounds adapted to in situ form such carboxylate, in the presence of a catalytically effective amount of a salt of a carboxylic acid, the carboxylic acid salt catalyst being an alkali metal carboxylate, an ammonium carboxylate or an alkaline earth metal carboxylate.

2. The process as defined in claim 1, the alkyl moiety of said alkyl carboxylate being linear or branched chain and containing from 1 to 6 carbon atoms, and the alkenyl moiety of said alkenyl carboxylate being linear or branched chain and containing from 3 to 6 carbon atoms.

3. The process as defined by claim 1, wherein Ar is benzene, naphthalene, anthracene or phenanthrene; the substituents R, which are identical or different, represent a hydroxyl group, a linear or branched chain alkyl radical having from 1 to 4 carbon atoms, a linear or branched chain alkenyl radical having 2 to 4 carbon atoms, a phenyl radical, a phenyl radical substituted with one or more alkyl radicals each having 1 to 4 carbon atoms, a cyclohexyl radical, a cyclohexyl radical substituted with one or more alkyl radicals each having 1 to 4 carbon atoms, a phenylalkyl radical in which the aliphatic chain contains 1 to 3 carbon atoms, a cyclohexyl-alkyl radical in which the aliphatic chain contains 1 to 3 carbon atoms, a chlorine atom, a bromine atom or a nitro group; and n is an integer ranging from 0 to 3.

4. The process as defined by claim 3, the compound (I) being pyrocatechol, resorcinol, hydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene or 2,7-dihydroxynaphthalene.

5. The process as defined by claim 1, wherein Ar represents benzene or naphthalene; the substituents R, which are identical or different, represent a hydroxyl group, a linear or branched chain alkyl radical having 2 to 4 carbon atoms, a linear or branched chain alkenyl radical having 2 to 4 carbon atoms, a chlorine atom, a bromine atom or a nitro group; and n is 1, 2 or 3.

6. The process as defined by claim 5, the compound (I) being resorcinol, pyrocatechol, hydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, pyrogallol, 1,2,4-trihydroxybenzene, 1-bromo-2,4-dihydroxybenzene, 1-bromo-3,5-dihydroxybenzene, 2-bromo-1,3-dihydroxybenzene, 2-bromo-1,4-dihydroxybenzene, 4-bromo-1,2-dihydroxybenzene, 1-butyl-2,4-dihydroxybenzene, 1-chloro-2,3-dihydroxybenzene, 1-chloro-2,4-dihydroxybenzene, 1-chloro-3,5-dihydroxybenzene, 2-chloro-1,3-dihydroxybenzene, 2-chloro-1,4-dihydroxybenzene, 4-chloro-1,2-dihydroxybenzene, 2,4-dihydroxy-1-ethylbenzene, 2,4-dihydroxy-1-isobutylbenzene, 1,2-dihydroxy-4-isopropylbenzene, 1,4-dihydroxy-2-isopropylbenzene, 2,4-dihydroxy-1-isopropylbenzene, 2,3-dihydroxy-1-isopropyl-4-methylbenzene, 1,4-dihydroxy-2-isopropyl-5-methylbenzene, 1,2-dihydroxy-3-methylbenzene, 1,3-dihydroxy-2-methylbenzene, 1,3-dihydroxy-2-nitrobenzene, 1,4-dihydroxy-2-nitrobenzene, 1,2-dihydroxy-4-propylbenzene, 1,3-dihydroxy-5-propylbenzene, 2,4-dihydroxy-1-propylbenzene, 1,2-dichloro-4,5-dihydroxybenzene, 1,3-dichloro-2,5-dihydroxybenzene, 1,4-dichloro-2,5-dihydroxybenzene, 1,5-dichloro-2,3-dihydroxybenzene, 1,5-dichloro-2,4-dihydroxybenzene, 2,3-dichloro-1,4-dihydroxybenzene, 1,2-dihydroxy-3,5-dimethylbenzene, 1,2-dihydroxy-4,5-dimethylbenzene, 1,3-dihydroxy-2,4-dimethylbenzene, 1,3-dihydroxy-2,5-dimethylbenzene, 1,4-dihydroxy-2,3-dimethylbenzene, 1,4-dihydroxy-2,5-dimethylbenzene, 1,5-dihydroxy-2,4-dimethylbenzene, 1,5-dihydroxy-3,4-dimethylbenzene, 2,5-dihydroxy-1,3-dimethylbenzene, or 1,3-dihydroxy-2,4-dinitrobenzene.

7. The process as defined by claim 5, the compound (I) being pyrocatechol.

8. The process as defined by claim 5, wherein n is 1.

9. The process as defined by claim 5, wherein n is 2.

10. The process as defined by claim 5, wherein n is 3.

11. The process as defined by claim 1, 3, 4, 5, 6 or 7, the monoetherification being with a carboxylate, said carboxylate being an ester of a monofunctional saturated or unsaturated aliphatic carboxylic acid containing from 2 to 18 carbon atoms, or of a polyfunctional saturated or unsaturated aliphatic carboxylic acid containing from 3 to 18 carbon atoms, or of a monofunctional or polyfunctional aromatic acid, or of a monofunctional or polyfunctional arylaliphatic acid, or of a monofunctional or polyfunctional cycloaliphatic acid, with methanol, ethanol, n-propanol, isopropanol, butan-1-ol, butan-2-ol, tert.-butanol, prop-2-en-1-ol, 2-methylprop-2-en-1-ol, but-2-en-1-ol, but-3-en-1-ol or but-3-en-2-ol.

12. The process as defined by claim 1, 3, 4, 5, 6 or 7, the monoetherification being with a carboxylate-forming admixture, said admixture comprising methanol, ethanol, n-propanol, isopropanol, butan-1-ol, butan-2-ol, tert.-butanol, prop-2-en-1-ol, 2-methylprop-2-en-1-ol, but-2-en-1-ol, but-3-en-1-ol or but-3-en-2-ol, and a monofunctional saturated or unsaturated aliphatic carboxylic acid containing from 2 to 18 carbon atoms, a polyfunctional saturated or unsaturated aliphatic carboxylic acid containing from 3 to 18 carbon atoms, a monofunctional or polyfunctional aromatic acid, a monofunctional or polyfunctional arylaliphatic acid, or a monofunctional or polyfunctional cycloaliphatic acid.

13. The process as defined by claim 12, wherein the molar ratio alcohol/carboxylic acid ranges from 0.02 to 50.

14. The process as defined by claim 11, the carboxylic acid moiety of the carboxylate being a monofunctional or difunctional saturated aliphatic acid having from 2 to 6 carbon atoms, benzoic acid or ortho-phthalic, metaphthalic or terephthalic acid.

15. The process as defined by claim 12, the carboxylic acid comprising the carboxylate-forming admixture being a monofunctional or difunctional saturated aliphatic acid having from 2 to 6 carbon atoms, benzoic acid or ortho-phthalic, metaphthalic or terephthalic acid.

16. The process as defined by claim 1 or 5, wherein the carboxylic acid salt catalyst is a salt of a monofunctional or difunctional saturated aliphatic acid having 2 to 6 carbon atoms, of benzoic acid or of ortho-phthalic, meta-phthalic or terephthalic acid.

17. The process as defined by claim 1 or 5, wherein the monoetherification reaction is carried out in the presence of water.

18. The process as defined by claim 17, wherein the water constitutes from 1% to 95% by volume of the liquid reaction mixture.

19. The process as defined by claim 1 or 3, wherein the reaction mixture comprises a dicarboxylic acid, one acid function of which is free and the other is salified.

20. The process as defined by claim 1 or 5, the monoetherification reaction being carried out at a temperature ranging from 150° C. to 350° C.

21. The process as defined by claim 1, 3 or 5, wherein the molar ratio of the ester or alcohol comprising the carboxylate or carboxylate-forming admixture, to the phenolic compound (I), is at least 0.5.

22. The process as defined by claim 21, said ratio being at least 1.

23. The process as defined by claim 1 or 5, the catalyst being an alkali metal carboxylate.

24. The process as defined by claim 1, 3 or 5, the carboxylic acid comprising the catalyst and the monoetherifying carboxylate being the same.

25. The process as defined by claim 1 or 5, the catalyst being sodium acetate.

26. A process for the monoetherification of a phenol, comprising selectively monoetherifying a phenolic hydroxyl group of a compound having the structural formula (I):

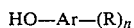

HO—Ar—(R)$_n$   (I)

wherein Ar is an aryl radical comprising a benzene ring, or a plurality of ortho-fused or ortho- and peri-fused benzene rings: the substituents R, which are identical or different, represent a hydroxyl group, a linear or branched chain alkyl radical having from 1 to 6 carbon atoms, a linear or branched chain alkenyl radical having from 2 to 6 carbon atoms, a phenyl radical, a phenyl radical substituted with one or more alkyl radicals each having 1 to 4 carbon atoms, a cycloalkyl radical containing 5 or 6 carbon atoms, a cycloalkyl radical containing 5 or 6 carbon atoms and substituted with one or more alkyl radicals each having 1 to 4 carbon atoms, a phenylalkyl radical in which the aliphatic chain contains 1 to 4 carbon atoms, a cycloalkyl-alkyl radical in which the cycloalkyl portion contains 5 or 6 carbon atoms and the aliphatic chain contains from 1 to 4 carbon atoms, a halogen atom, a nitro group, an amine group, an aldehyde group or a nitrile group, at least one of the substituents R being a hydroxyl group; and n is a number ranging from 1 to 5; with an alkyl or alkenyl carboxylate, or admixture of compounds adapted to in situ form such carboxylate, in the presence of a catalytically effective amount of (a) a salt of a carboxylic acid, the carboxylic acid salt catalyst being an alkali metal carboxylate, an ammonium carboxylate or an alkaline earth metal carboxylate, and (b) an inorganic halide, the inorganic halide being an alkali metal iodide, an alkaline earth metal iodide or ammonium iodide.

27. The process as defined by claim 26, wherein the inorganic halide is sodium iodide.

28. The process as defined by claim 26, wherein the inorganic halide is potassium iodide.

29. The process as defined by claim 26, 27 or 28, wherein the weight ratio inorganic halide/phenolic compound (I) ranges from 0.01 to 50.

30. The process as defined by claim 29, wherein the weight ratio inorganic halide/phenolic compound (I) ranges from 0.05 to 20.

31. The process as defined by claim 26, the alkyl moiety of said alkyl carboxylate being linear or branched chain and containing from 1 to 6 carbon atoms, and the alkenyl moiety of said alkenyl carboxylate being linear or branched chain and containing from 3 to 6 carbon atoms.

32. The process as defined by claim 26, wherein Ar is benzene, naphthalene, anthracene or phenanthrene; the substituents R, which are identical or different, represent a hydroxyl group, a linear or branched chain alkyl radical having from 1 to 4 carbon atoms, a linear or branched chain alkenyl radical having 2 to 4 carbon atoms, a phenyl radical, a phenyl radical substituted with one or more alkyl radicals each having 1 to 4 carbon atoms, a cyclohexyl radical, a cyclohexyl radical substituted with one or more alkyl radicals each having 1 to 4 carbon atoms, a phenylalkyl radical in which the aliphatic chain contains 1 to 3 carbon atoms, a cyclohexyl-alkyl radical in which the aliphatic chain contains 1 to 3 carbon atoms, a chlorine atom, a bromine atom or a nitro group; and n is an integer ranging from 1 to 3.

33. The process as defined by claim 32, the compound (I) being pyrocatechol, resorcinol, hydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene or 2,7-dihydroxynaphthalene.

34. The process as defined by claim 26, wherein Ar represents benzene or naphthalene; the substituents R, which are identical or different, represent a hydroxyl group, a linear or branched chain alkyl radical having 2 to 4 carbon atoms, a linear or branched chain alkenyl radical having 2 to 4 carbon atoms, a chlorine atom, a bromine atom or a nitro group; and n is 1, 2 or 3.

35. The process as defined by claim 34, the compound (I) being resorcinol, pyrocatechol, hydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, pyrogallol, 1,2,4-trihydroxybenzene, 1-bromo-2,4-dihydroxybenzene, 1-bromo-3,5-dihydroxybenzene, 2-bromo-1,3-dihydroxybenzene, 2-bromo-1,4-dihydroxybenzene, 4-bromo-1,2-dihydroxybenzene, 1-butyl-2,4-dihydroxybenzene, 1-chloro-2,3-dihydroxybenzene, 1-chloro-2,4-dihydroxybenzene, 1-chloro-3,5-dihydroxybenzene, 2-chloro-1,3-dihydroxybenzene, 2-chloro-1,4-dihydroxybenzene, 4-chloro-1,2-dihydroxybenzene, 2,4-dihydroxy-1-ethylbenzene, 2,4-dihydroxy-1-isobutylbenzene, 1,2-dihydroxy-4-isopropylbenzene, 1,4-dihydroxy-2-isopropylbenzene, 2,4-dihydroxy-1-isopropylbenzene, 2,3-dihydroxy-1-isopropyl-4-methylbenzene, 1,4-dihydroxy-2-isopropyl-5-methylbenzene, 1,2-dihydroxy-3-methylbenzene, 1,3-dihydroxy-2-methylbenzene, 1,3-dihydroxy-2-nitrobenzene, 1,4-dihydroxy-2-nitrobenzene, 1,2-dihydroxy-4-propylbenzene, 1,3-dihydroxy-5-propylbenzene, 2,4-dihydroxy-1-propylbenzene, 1,2-dichloro-4,5-dihydroxybenzene, 1,3-dichloro-2,5-dihydroxybenzene, 1,4-dichloro-2,5-dihydroxybenzene, 1,5-dichloro-2,3-dihydroxybenzene, 1,5-dichloro-2,4-dihydroxybenzene, 2,3-dichloro-1,4-dihydroxybenzene, 1,2-dihydroxy-3,5-dimethylbenzene, 1,2-dihydroxy-4,5-dimethylbenzene, 1,3-dihydroxy-2,4-dimethylbenzene, 1,3-dihydroxy-2,5-dimethylbenzene, 1,4-dihydroxy-2,3-dimethylbenzene, 1,4-dihydroxy-2,5-dimethylbenzene, 1,5-dihydroxy-2,4-dimethylbenzene, 1,5-dihydroxy-3,4-dimethylbenzene, 2,5-dihydroxy-1,3-dimethylbenzene, or 1,3-dihydroxy-2,4-dinitrobenzene.

36. The process as defined by claim 26, 32 or 34, the monoetherification being with a carboxylate, said carboxylate being an ester of a monofunctional saturated or unsaturated aliphatic carboxylic acid containing from 2 to 18 carbon atoms, or of a polyfunctional saturated or unsaturated aliphatic carboxylic acid containing from 3 to 18 carbon atoms, or of a monofunctional or polyfunctional aromatic acid, or of a monofunctional or polyfunctional arylaliphatic acid, or of a monofunctional or polyfunctional cycloaliphatic acid, with methanol, ethanol, n-propanol, isopropanol, butan-1-ol, butan-2-ol, tert.-butanol, prop-2-en-1-ol, 2-methylprop-2-en-1-ol, but-2-en-1-ol, but-3-en-1-ol or but-3-en-2-ol.

37. The process as defined by claim 26, 32 or 34, the monoetherification being with a carboxylate-forming admixture, said admixture comprising methanol, ethanol, n-propanol, isopropanol, butan-1-ol, butan-2-ol, tert.-butanol, prop-2-en-1-ol, 2-methylprop-2-en-1-ol, but-2-en-1-ol, but-3-en-1-ol or but-3-en-2-ol, and a monofunctional saturated or unsaturated aliphatic carboxylic acid containing from 2 to 18 carbon atoms, a polyfunctional saturated or unsaturated aliphatic carboxylic acid containing from 3 to 18 carbon atoms, a monofunctional or polyfunctional aromatic acid, a monofunctional or polyfunctional arylaliphatic acid, or a monofunctional or polyfunctional cycloaliphatic acid.

38. The process as defined by claim 37, wherein the molar ratio alcohol/carboxylic acid ranges from 0.02 to 50.

39. The process as defined by claim 36, the carboxylic acid moiety of the carboxylate being a monofunctional or difunctional saturated aliphatic acid having from 2 to 6 carbon atoms, benzoic acid or ortho-phthalic, meta-phthalic or terephthalic acid.

40. The process as defined by claim 37, the carboxylic acid comprising the carboxylate-forming admixture being a monofunctional or difunctional saturated aliphatic acid having from 2 to 6 carbon atoms, benzoic acid or ortho-phthalic, meta-phthalic or terephthalic acid.

41. The process as defined by claim 26 or 34, wherein the carboxylic acid salt catalyst is a salt of a monofunctional or difunctional saturated aliphatic acid having 2 to 6 carbon atoms, of benzoic acid or of ortho-phthalic, meta-phthalic or terephthalic acid.

42. The process as defined by claim 26 or 34, wherein the monoetherification reaction is carried out in the presence of water.

43. The process as defined by claim 42, wherein the water constitutes from 1% to 95% by volume of the liquid reaction mixture.

44. The process as defined by claim 26 or 32, wherein the reaction mixture comprises a dicarboxylic acid, one acid function of which is free and the other is salified.

45. The process as defined by claim 26 or 34, the monoetherification reaction being carried out at a temperature ranging from 150° C. to 350° C.

46. The process as defined by claim 26, 32 or 34, wherein the molar ratio of the ester or alcohol comprising the carboxylate or carboxylate-forming admixture, to the phenolic compound (I), is at least 0.5.

47. The process as defined by claim 46, said ratio being at least 1.

48. The process as defined by claim 26 or 34, the carboxylic acid salt catalyst being an alkali metal carboxylate.

49. The process as defined by claim 26, 32 or 34, the carboxylic acid comprising the carboxylic acid salt catalyst and the monoetherifying carboxylate being the same.

50. The process as defined by claim 26 or 34, the carboxylic acid salt catalyst being sodium acetate.

51. The process as defined by claim 26 or 34, the carboxylic acid salt catalyst being an alkali metal carboxylate and the inorganic halide co-catalyst being an alkali metal iodide.

52. The process as defined by claim 26 or 34, the carboxylic acid salt catalyst being sodium acetate and the inorganic halide co-catalyst being potassium iodide.

* * * * *